United States Patent [19]

Blasnik et al.

[11] Patent Number: 5,217,004
[45] Date of Patent: Jun. 8, 1993

[54] INHALATION ACTUATED DISPENSING APPARATUS

[75] Inventors: William Blasnik, Fort Lee; Robert M. Whittemore, Jr., New Milford, both of N.J.

[73] Assignee: Tenax Corporation, Danbury, Conn.

[21] Appl. No.: 626,732

[22] Filed: Dec. 13, 1990

[51] Int. Cl.$^5$ .................................. A61M 11/00
[52] U.S. Cl. ........................ 128/200.23; 128/200.14
[58] Field of Search ................. 128/200.14, 200.23, 128/207.16, 203.12

[56] References Cited

U.S. PATENT DOCUMENTS

| 3,187,748 | 6/1965 | Mitchell . | |
|---|---|---|---|
| 3,456,644 | 7/1969 | Thiel . | |
| 3,565,070 | 2/1971 | Hanson . | |
| 3,598,294 | 8/1971 | Hedrick . | |
| 3,605,738 | 9/1971 | Ciranna . | |
| 3,636,949 | 1/1972 | Kropp . | |
| 3,732,864 | 5/1973 | Thompson . | |
| 3,789,843 | 2/1974 | Armstrong . | |
| 3,814,297 | 6/1974 | Warren . | |
| 4,414,972 | 11/1983 | Young et al. | 128/200.23 |
| 4,648,393 | 3/1987 | Landis . | |
| 4,664,107 | 5/1987 | Wass . | |
| 4,955,371 | 9/1990 | Zamba et al. | 128/200.18 |

Primary Examiner—Edgar S. Burr
Assistant Examiner—K. L. Asher
Attorney, Agent, or Firm—James & Franklin

[57] ABSTRACT

Movement of the cover relative to the housing spring loads and latches a piston carrier in the armed position. Inhalation causes a passageway door to open, releasing the carrier latch to permit the carrier to be moved toward the canister by the spring. The piston moves with the carrier, due to a fluid connection therebetween, applying a compression force on the spring loaded canister valve stem and causing it to dispense the inhalant through an opening in the piston which functions as a nozzle. After the inhalant is dispensed, the carrier fluid vents permitting the spring of the canister valve stem to move the piston relative to the carrier, and thus release the force applied to the valve stem by the piston. The sensitivity of the toggle linkage between the door and the carrier latch is adjustable. The linkage can be manually tripped for testing purposes.

22 Claims, 5 Drawing Sheets

INHALATION ACTUATED DISPENSING APPARATUS

The present invention relates to inhalation actuated devices for dispensing inhalants or the like from a pressurized inhalant containing canister, and more particularly to an inhalation actuated dispensing apparatus wherein valve stem leakage and damage is substantially reduced because no force is applied to the valve stem of the canister at any time other than during the brief period when the dispensing of the inhalant is occurring.

Many pharmaceuticals intended to be administered by inhalation are supplied in pressurized aerosol canisters which dispense a metered amount of inhalant when triggered by the actuation of a valve. The valve has an outwardly extending spring loaded valve stem upon which a manually depressible plastic nozzle is mounted. The nozzle serves as a force transfer member for the finger and to direct and shape the inhalant spray. It has an internal passageway with an axially extending section adapted to receive the valve stem and a section extending towards the side surface of the nozzle, usually having a conical configuration, so as to form a conical-shaped spray pattern. The nozzle is depressed by the finger to apply sufficient force on the valve stem, in a direction toward the canister, to actuate the valve.

Such manually operated spray devices may be difficult for certain individuals to use effectively because they require coordination of the breathing of the user with valve manipulation. Children, the elderly and individuals with other types of muscular coordination impairment may find it hard to actuate the device at the correct time. There is a tendency to overdose or underdose, both of which are disadvantageous and are results to be avoided when medicines are involved.

In order to overcome this problem, inhalation actuated dispensing devices have been developed. In general, such devices include a housing within which a moveable element is moved to a latched position against a compression spring. An air passageway in the housing is at least partially blocked by a vane or door. Upon inhalation on a mouthpiece, the door opens, unlatching the element. The spring urges the element to apply sufficient force to depress the valve stem to dispense the inhalant into a mouthpiece. Thus, a dose of inhalant is released in coordination with the inhalation of the patient.

However, pressurized canisters require a relatively large force, in the order of from four to eight pounds, to depress the valve stem completely against the internal spring to release the inhalant. Any automatic actuation device designed for use with such a canister must be capable of applying a force on the valve stem large enough to cause the required depression of the stem. This requires a relatively powerful spring.

In conventional automatic actuation devices, once the inhalant has been dispensed, the relatively powerful spring continues to urge the force applying element to apply the relatively large force on the valve stem. It is only after the device is rearmed, by latching the force applying element in the armed position that the force is released. The continuous application of such a large amount of force on the valve stem tends to cause unwanted discharge or leakage of the inhalant and may eventually result in permanent deformation of the valve stem or damage to the internal valve stem spring.

Moreover, the travel distance between the extended and depressed positions of the valve stem is quite small, on the order of 0.08 inch. This requires that the force applying element be moved with extreme accuracy to avoid depressing the valve stem beyond its limit, which can also result in permanent damage to the valve.

Another problem associated with inhalation actuated dispensing devices, in particular, is the setting of the amount of inhalation force necessary to release the latch of the spring loaded force applying element. Setting the force at too high a level may prevent users with severe respiratory problems from being able to actuate the device. On the other hand, setting the force too low may result in frequent misfirings.

It is also desirable that the device be actuatable by means other than by inhalation, to permit the user to test the device without having to ingest the inhalant. It is further desirable that the canister be removable from the device to permit the user to ascertain the amount of inhalant remaining in the canister. Because the canister is opaque, this must be done by immersing the removed canister in a liquid and observing the level at which it floats.

The present invention overcomes the problems associated with the application of force on the valve stem through the use of a system in which the compression force applied to the valve stem is released immediately after the inhalant is sprayed. The only time any substantial force is applied to the valve stem is during that brief moment in which inhalant is being dispensed. No substantial force is applied at any other time. This being the case, the chances of accidental discharge or leakage of the inhalant or of damage to the valve stem or internal spring are greatly reduced.

Problems associated with setting the amount of force necessary to trip the carrier latch are solved through the use of a uniquely constructed toggle linkage which serves as a door actuated latch release for the force applying element. For testing purposes, a button is provided which is externally accessible to actuate the latch release. To permit the user to ascertain the amount of inhalant remaining in the canister, the canister may be easily removed from the device at any time, because it is held in place by resilient arms located below the removable housing cover.

The present invention overcomes the problems associated with the application of force on the valve stem through the use of a system in which the force applied to the valve stem to cause depression is released immediately after the inhalant is sprayed. Any substantial force applied to the valve stem is during that brief moment when inhalant is being dispensed. No substantial force is applied at any other time. This being the case, the chances of accidental release or leakage of the inhalant or of deformation of the valve stem are greatly reduced.

It is, therefore, a prime object of the present invention to provide an inhalation actuated dispensing apparatus in which substantial force is applied to the canister valve stem only at the moment in which the valve stem is depressed to dispense the inhalant.

It is another object of the present invention to provide an inhalation actuated dispensing apparatus which includes a dash-pot type assembly for releasing the force applied to the valve stem immediately after the inhalant is dispensed.

It is another object of the present invention to provide an inhalation actuated dispensing apparatus which includes a fluid connection between the force applying element and the carrier which moves the element against the valve stem to cause them to move as a unit.

It is another object of the present invention to provide an inhalation actuated dispensing apparatus which includes means for releasing the fluid connection to permit the force applying element to move relative to the carrier.

It is another object of the present invention to provide an inhalation actuated dispensing apparatus in which the relative position of the housing and carrier members indicates whether the apparatus is in the armed or disarmed state.

It is another object of the present invention to provide an inhalation actuated dispensing apparatus which includes a toggle linkage between the air passageway door and the latch for the carrier in which the amount of inhalation force required for actuation can be set at minimal levels with extreme accuracy.

It is another object of the present invention to provide an inhalation actuated dispensing apparatus which includes a manually actuatable mechanism which permits the testing of the device.

It is another object of the present invention to provide an inhalation actuated dispensing apparatus in which the canister is releasably retained in the housing to permit removal thereof to ascertain the amount of inhalant in the canister.

It is another object of the present invention to provide an inhalation actuated dispensing apparatus which is comprised of a relatively small number of relatively simple parts that function reliably together and which are relatively inexpensive to manufacture and assemble.

In accordance with the present invention, an inhalation actuated dispensing apparatus is provided for use with a pressurized inhalant containing canister of the type having a moveable discharge valve stem which is normally spring loaded toward a charged position and is adapted to dispense a measured dose of inhalant when moved to a discharge position against the action of the internal valve stem spring. The apparatus includes a housing into which the canister is received. Means, effective when actuated by inhalation, are provided for applying a force on the valve stem of sufficient magnitude to move the valve stem toward its discharge position and for automatically releasing the applied force after the inhalant has been dispensed.

The force applying and releasing means comprises piston means aligned with the valve stem, means moveable relative to the housing for carrying the piston means and means for operably connecting the piston means and the carrier means for movement as a unit and to permit relative movement therebetween. The carrier means is moveable relative to the housing between an armed position relatively remote from the canister and a disarmed or resting position relatively close to the canister. Means are provided for urging the carrier means towards the disarmed position.

Means are provided to latch the carrier means in the armed position, against the force of the urging means. The carrier means is released in response to inhalation by the user to permit the urging means to move the carrier means from the armed position toward the disarmed position.

The connecting means connects the piston means and the carrier means such that the piston means moves with the carrier means as a unit as the carrier means is moved from its armed position toward its disarmed position. However, the connecting means permits the piston means to move relative to the carrier means to release the force applied on the valve stem, after the piston means has moved the valve stem to its discharge position.

The connecting means preferably comprises fluid connecting means in the form of a sealed fluid reservoir operably interposed between the carrier means and the piston means and a fluid vent situated in the carrier means. The carrier means includes a body having a bore into which the piston means is movably received. The bore and the piston means define the fluid reservoir. The fluid in the reservoir causes the piston to move with the carrier means as a unit as the carrier means moves toward its disarmed position because it moves so quickly. The vent permits the fluid to escape from the reservoir to permit the piston means to move relative to the carrier means to release the force applied on the valve stem by the piston means, after the carrier means moves to the disarmed position.

The housing has an air passageway. The latch means includes a door mounted on the housing for movement between a position substantially obstructing the passageway and a substantially non-obstructing position. The latch means further includes toggle means operably connecting the carrier means and the housing. The toggle means is moveable between a latched position, wherein the carrier means is retained in the armed position, and a release position wherein the carrier means latch is released. Means are provided for operably latching the toggle means and the door.

The toggle means comprise a first element and a second element. Means are provided for pivotally mounting one end of the first element on the carrier means for movement about a first axis. Means are provided for pivotally mounting one end of the second element on the housing for movement about a second axis. Means are provided for pivotally connecting the other end of the first element and the other end of the second element.

The door and the toggle means connecting means retain the toggle means in a latched position when the door is in the substantially obstructing position. In the latched position, the first axis, the second axis and the axis of the first and second element connecting means are substantially co-linearly aligned.

The housing includes first and second parts movable relative to each other to move the carrier means from the disarmed position to the armed position, against the action of the urging means. One of the housing parts is adapted to enclose the canister. The other part includes means for removably retaining the canister.

The piston means includes nozzle means adapted to align with the valve stem. The nozzle means includes a channel adapted to receive the inhalant dispensed from the valve stem. The channel has a section elongated in the direction of the valve stem axis and a conical section having an axis extending in a direction approximately perpendicular to the valve stem axis.

Means are provided for manually releasing the toggle linkage latching means. The manual releasing means is preferably an externally accessible button.

To these and such other objects which may hereinafter appear, the present invention relates to an inhalation actuated dispensing apparatus as described in detail in the following specification, and recited in the annexed claims, taken together with the accompanying drawings, where like numerals refer to like parts, and in which:

Figure 1:
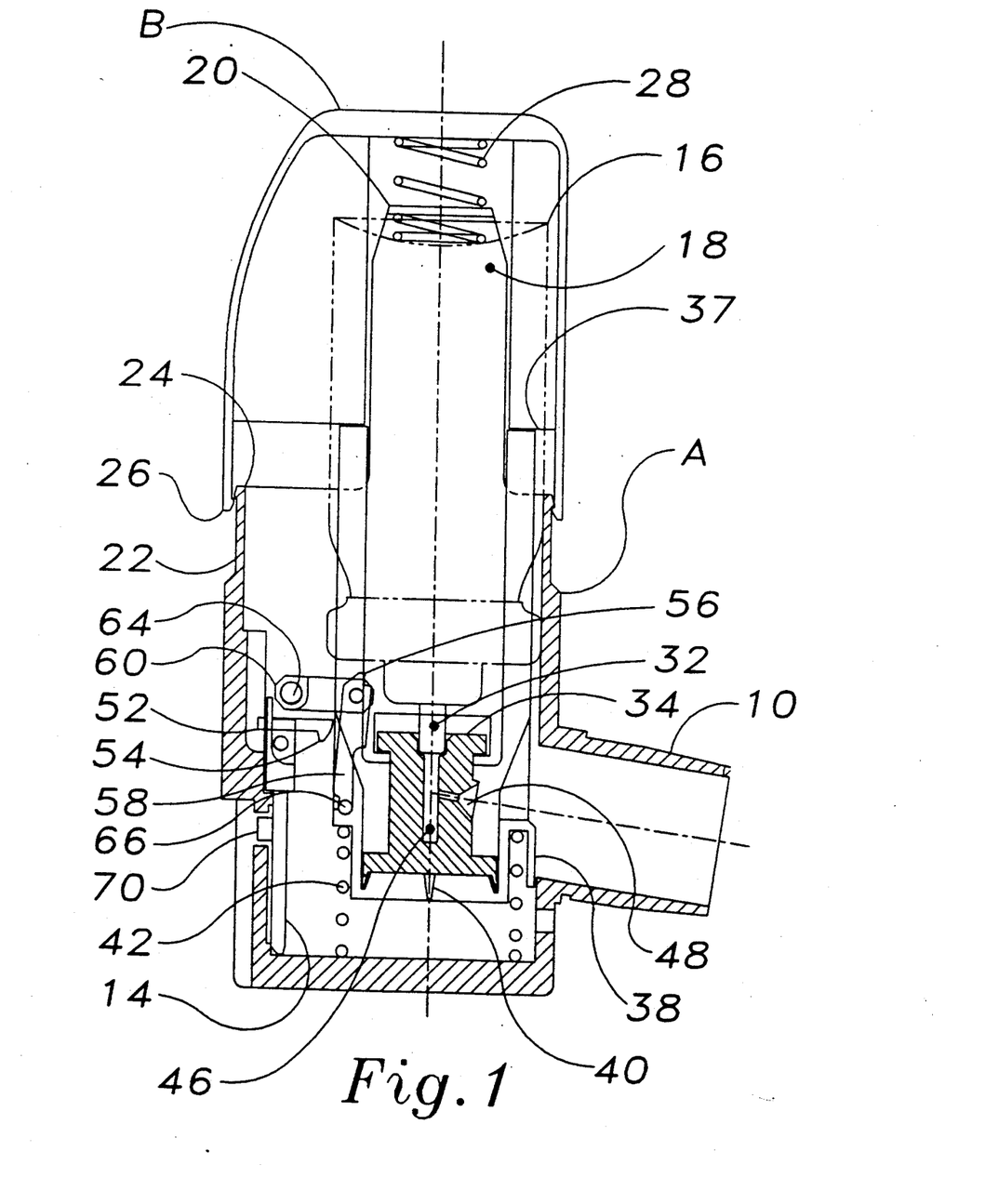
FIG. 1 is a side cross sectional view of the device with the parts shown in the rest position.

As seen in FIG. 1, the device of the present invention comprises a hollow housing base, generally designated A, into which the pressurized inhalant containing canister is removably received. A cover member, generally designated B, encloses the canister and is removably and movably mounted on housing base A.

The front on housing base A is provided with a protruding hollow mouthpiece 10 which is received in the mouth of the user. An air passageway extends through housing base A between mouthpiece 10 and an opening 12 in the rear of the housing base. Opening 12 is normally obstructed by a door 14.

As seen in FIG. 1, canister 16 is held in place in housing base A by two resilient arms 18 which have inwardly extending portions 20 which will normally lodge adjacent to the top of the canister to retain the canister in housing base A. Arms 18 can be manually separated to release the canister from the base.

Figure 2:
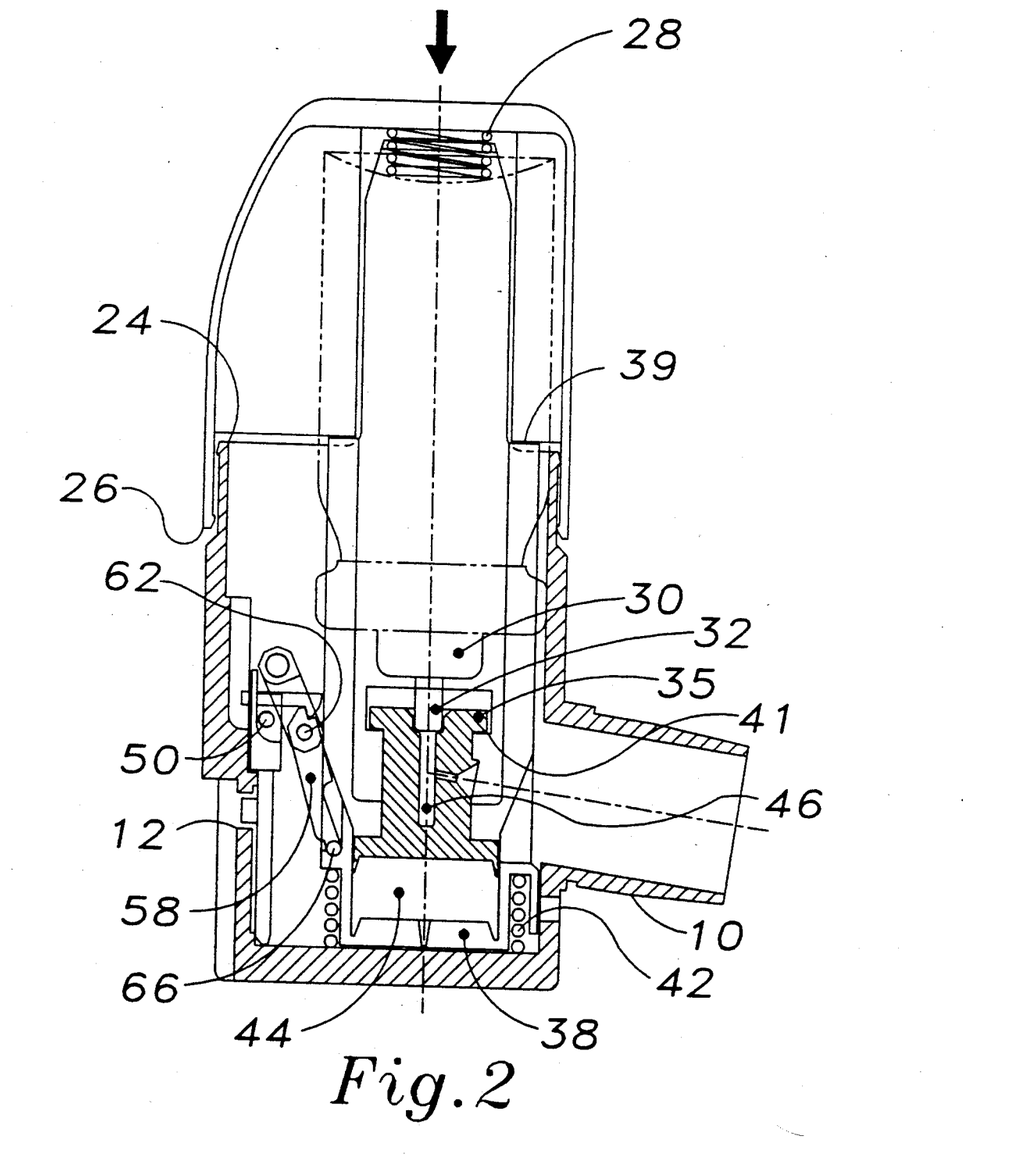
FIG. 2 is a side cross sectional view of the device with the parts shown as the device is being armed.
Figure 3:
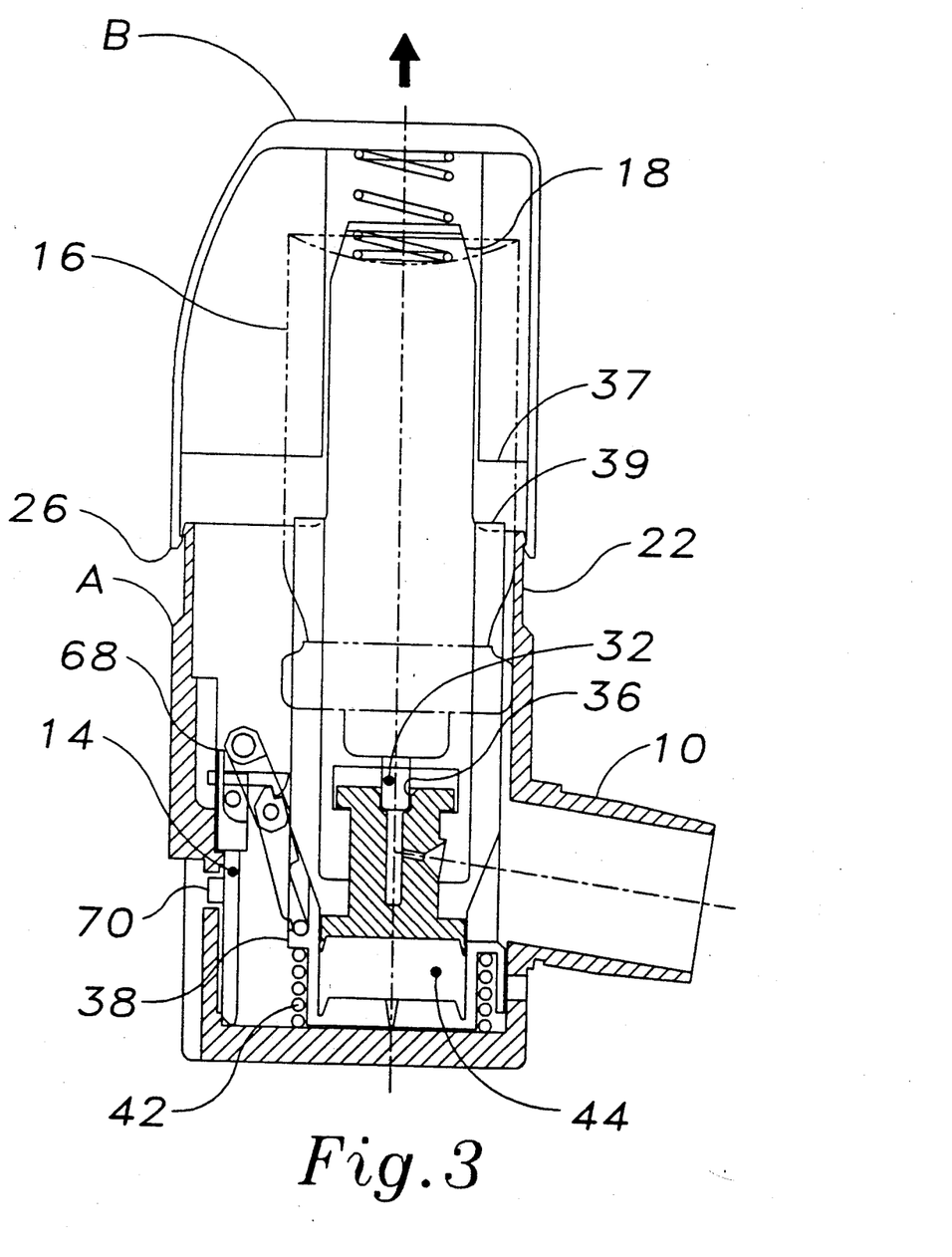
FIG. 3 is a side cross sectional view of the device with the parts shown as the device is in the armed position.

Cover B is movable relative to housing base A, between the position shown in FIG. 1 and the position shown in FIG. 2, in order to arm the device. The maximum length of the relative movement between the base and cover is determined by a circumferential recess 22 on the exterior of housing base A. Interlocking beads 24, 26 are provided on the housing base and cover, respectively, to define the extreme relative position of the cover and base and to permit the cover to snap fit onto the housing base. A canister spring 28 is provided between the bottom of the canister and the interior surface of cover B. As seen in FIG. 2, spring 28 is compressed as the device is being armed. Once armed, spring 28 moves cover B away from housing base A until beads 24,26 interlock, as shown in FIG. 3.

Canister 16 has a neck 30 from which an internally spring loaded valve stem 32 extends. Valve stem 32 is normally "charged" in its extended position (FIGS. 1, 2, and 3) but when depressed (FIG. 5) will "fire" to dispense a measured dose of inhalant.

The element which applies the force on valve stem 32 is made up of two parts. Piston 34 is the part which is adjacent stem 32 and has a recess 36 into which stem 32 is received. Piston 34 is situated within the recess of a cup shaped carrier 38. Carrier 38 has a vent opening 40 through its bottom surface. Piston 34 is movable with carrier 38 as a unit and relative to carrier 38 as well. The relative position of these parts is governed by a fluid connection formed between them. This connection is a result of the substantially air tight seal which the exterior flexible wall of the piston makes with the interior wall of the carrier. The parts will move together as a unit in order to depress the valve stem as the device is fired because this movement occurs too quickly for the air to be exhausted from the space between the piston and carrier. However, the piston will move relative to the carrier to release the force applied to the valve stem, after the device has been fired, because there is sufficient time for the air to exhaust through the vent opening. As the air exhausts, the piston can move relative to the carrier. The speed of the relative movement between the parts is controlled by the size of vent 40. Vent 40 is made small enough to prevent a significant amount of air from escaping from the space between the parts as the carrier is moved toward the canister to depress the valve stem. This occurs in approximately 100 milliseconds. However, it is large enough to permit a significant amount of air to escape within the range of approximately 0.5 to 3.0 seconds after firing.

FIG. 2 illustrates the arming process. The user presses down on the cover B with his palm. The cover inside wall 37 pushes carrier fingers 39 projecting above and connected to carrier 38, compressing spring 42. However piston 34 has ears 35 resting on housing ledge 41. Therefore, the piston is held stationary while the carrier 38 is moving to the armed position, creating fluid space 44.

Figure 4:
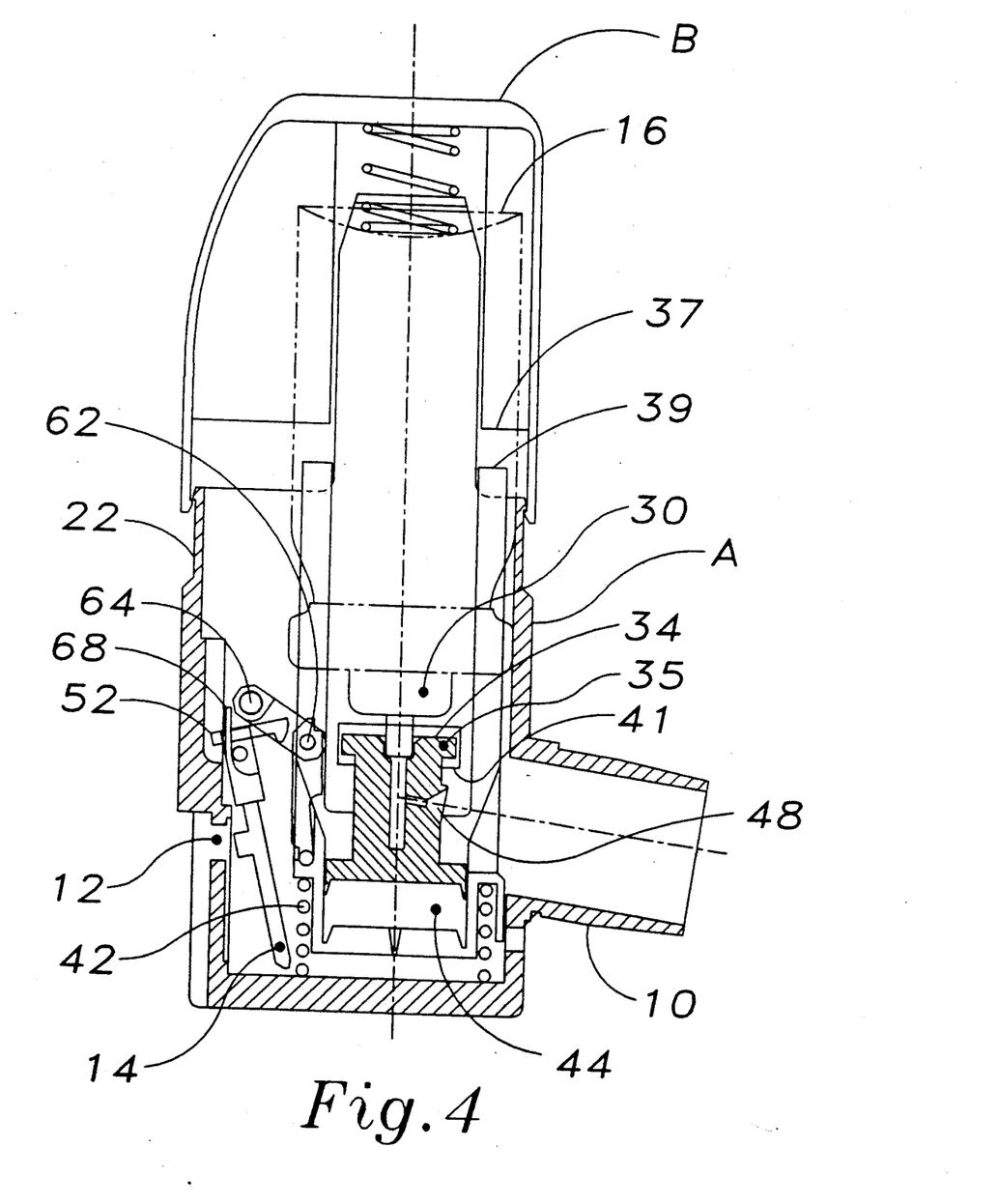
FIG. 4 is a side cross sectional view of the device with the parts shown as inhalation is occurring.
Figure 5:
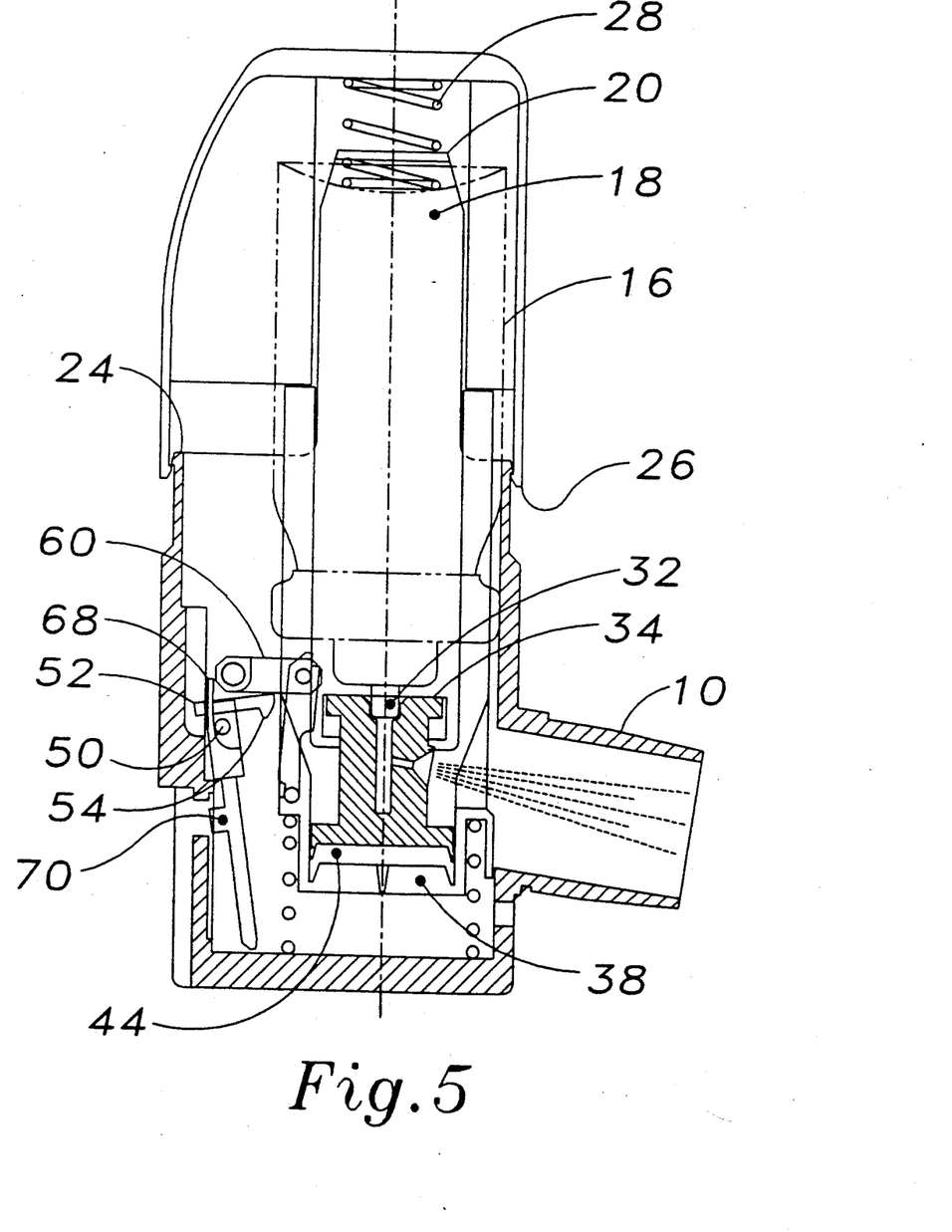
FIG. 5 is a side cross sectional view of the device with the parts shown in the fired position.

FIGS. 3, 4, and 5 illustrate the movement of the piston 34 and carrier 38. As shown in FIG. 3, in the armed state, carrier spring 42 has been compressed and carrier 38 is proximate the bottom of housing base A. Piston 34 is remote from the bottom of carrier 38. Space 44, between piston 36 and carrier 38, is filled with air.

As inhalation occurs, (FIG. 4), the door 14 is pushed away from housing A by the vacuum created. Door latch 54 separates from latching portion 56 of carrier link 58. Spring finger 68 urges door to return to vertical position, ready for next cycle. Carrier 38 is unlatched and spring 42 urges piston 34 and carrier 38 as a unit forcefully toward canister 16. Since this occurs relatively quickly (in approximately 0.1 second), the air in space 44 cannot escape through vent 40. Although the air may be compressed somewhat by the force, it acts as a connection between the carrier and the piston such that the force of spring 42 is transferred through carrier 38 to piston 34 and hence to valve stem 32, depressing the valve stem.

Depression of valve stem 32 causes a dose of inhalant to be released (FIG. 5) into the axial section 46 of a channel within piston 34. The axial section 46 is connected to a conical section 48. The latter guides and shapes the spray as it moves into mouthpiece 10.

Within a short period after firing, piston 34 will move, relative to carrier 38, downwardly and away from canister 16 as the air in space 44 vents, releasing the force applied to valve stem 32 and allowing the stem to once again assume its extended position. The internal spring within the valve causes movement of the stem and the adjacent piston 34.

Carrier 38 is latched in the armed position, as shown in FIG. 3, by a mechanical linkage which is connected to door 14. Door 14 is pivotally mounted on housing base A by pin 50 such that it can move from a closed position obstructing rear opening 12 (FIGS. 1, 2, and 3) to an open position, as shown in FIG. 4, as the user inhales through mouthpiece 10.

Affixed to the top of door 14 and extending in a direction generally perpendicular thereto, is carrier latch 52. Latch 52 has a downwardly extending projection 54 at the end thereof. Projection 54 is shaped to interlock with a reciprocally shaped portion 56 of a carrier link 58. Link 58 is pivotally connected with one end of a housing link 60 by a pin 62. The other end of housing link 62 is pivotally connected to the wall of housing base A by pin 64.

When the device is armed, door 14 is parallel to the path of movement of carrier 38. Latch 52 engages carrier link 58. The carrier link and the housing link are substantially coplanar, that is, the axis of pins 62 and 64 are approximately in the same plane with pin 66. When the toggle formed by housing link 60 and carrier link 58 is in this state, the carrier is latched.

The effective length of latch 52 determines the position of projection 54 and the alignment of links 58 and 60. The amount of force necessary to trip the toggle and release the carrier is minimal when the links are coplaner. The length of latch 52 can be pre-set or made adjustable. While arming, carrier link 58 lifts latch 52 and then moves underneath it to permit projection 54 to engage portion 56 of the latch. The curved surfaces of each of these parts cooperate to achieve this position smoothly.

As will be appreciated, the more accurate the effective length of latch 52, the less force will be required to open the door and trip the toggle. The latched position is illustrated in FIGS. 2, and 3.

When door 14 is moved inwardly as air rushes through opening 12 to fill the partial vacuum created as the user inhales through mouthpiece 10, latch 52 is moved away from link 58, releasing the toggle such that the links move relative to each other about pin 62 (FIG. 4). This unlatches carrier 38 so it (and piston 34) can be moved toward canister 16 by spring 42. Pushing cover B toward housing base A recompresses spring 42 and resets the toggle to again latch the carrier in the armed position.

A button 70 on door 14 is accessible though the opening 12 in the rear of housing base A and when pressed will manually trip the toggle to release the carrier latch. This mechanism is provided to permit testing of the device without the necessity of inhaling the inhalant.

It should now be appreciated that one important aspect of the present invention relates to a breath actuated inhalant dispensing device which employs a means for applying force on a spring loaded canister which releases the force on the valve stem almost immediately after firing. Accordingly, the only time substantial force is applied to the valve stem is as the device is being fired.

While the particular preferred embodiment of the force applying element disclosed herein includes a dashpot arrangement, this aspect of the present invention should not be construed as being limited to this particular structure alone. Instead, this aspect of the present invention should be considered broad enough to include any linkage which can permit movement of parts of the force applying element as a unit to transmit force to the valve stem and thereafter permit the part adjacent the valve stem to move relative to its carrier, and away from the canister, to release the force on the stem. For example, a releasable toggle linkage between the piston and carrier is another structure which might be suitable for this task. Some types of proportional resistance governor devices might also be used.

Other aspects of the invention include the adjustability of the sensitivity of the door latch and the structure of the toggle linkage, the housing arms which permit removeability of the canister, and the manual testing feature. It should be appreciated that many variations and modifications to the various structures are possible and that all such variations and modifications which fall with the present invention are intended to be covered by the following claims:

We claim:

1. Inhalation actuated dispensing apparatus for use with a pressurized inhalant containing canister of the type having a discharge valve stem, normally spring loaded toward a charged position and adapted to dispense a measured dose of inhalant when moved to a discharged position, upon application of sufficient force against the action of a valve stem spring, said apparatus comprising a housing adapted to receive a canister, piston means moveable relative to said housing from a first position toward a second position, said piston means being adapted to apply a force on a valve stem of a canister when in said second position sufficient to move a valve stem toward its discharged position, in response to inhalation by the user, said piston means returning to said first position to automatically release said applied force, after the inhalant has been dispensed, carrier means for said piston means, said carrier means being moveable relative to said housing between an armed position, relatively remote from a canister received within said housing, and a disarmed position, relatively close to a canister received within said housing, means for urging said carrier means towards said disarmed position, means for operably connecting said piston means and said carrier means for movement as a unit and for relative movement therebetween, means for latching said carrier means in said armed position, against the force of said urging means and for releasing said carrier means, in response to inhalation by the user, to permit said urging means to move said carrier means from said armed position toward said disarmed position.

2. The apparatus of claim 1 wherein said connecting means connects said piston means and said carrier means such that said piston means and said carrier means move substantially as a unit as said carrier means is moved from its armed position toward its disarmed position.

3. The apparatus of claim 2 wherein said connecting means connects said piston means and said carrier means to permit said piston means to move relative to said carrier means, to release said applied force after said carrier means has moved to said disarmed position.

4. The apparatus of claim 3 wherein said connecting means comprises fluid connecting means.

5. The apparatus of claim 4 wherein said fluid connecting means comprises a reservoir of fluid operably interposed between said carrier means and said piston means and wherein said carrier means or said piston means contains a fluid vent.

6. The apparatus of claim 5 wherein said carrier means comprises a body having a recess into which said piston means is sealingly received, said body and said piston means defining said reservoir.

7. The apparatus of claim 5 wherein fluid in said reservoir causes said piston means and said carrier means to move substantially as a unit as said carrier means moves towards it disarmed position.

8. The apparatus of claim 5 wherein said vent permits a sufficient amount of said fluid to escape from said reservoir so as to permit said piston means to move toward said first position to release said applied force after said carrier means moves to said disarmed position.

9. The apparatus of claim 1 wherein said connecting means connects said piston means and said carrier means to permit said piston means to move relative to said carrier means, to release said applied force after said carrier means has moved to said disarmed position.

10. Inhalation actuated dispensing apparatus for use with a pressurized inhalant containing canister of the type having a moveable discharge valve stem, normally spring loaded toward a charged position, and adapted to dispense a measured dose of inhalant when moved to a discharged position against the action of a valve stem spring, said apparatus comprising a housing adapted to receive a canister, means adapted to contact a valve stem of a canister, apply a force thereto to move same from its charged position toward its discharged position and for automatically releasing said applied force after the inhalant has been dispensed, said valve stem contact means comprising piston means, said apparatus further comprising carrier means for said piston means, said carrier means being situated in said housing and moveable relative thereto between an armed position, wherein no substantial force is applied on a valve stem by said piston means and a disarmed position, means for urging said carrier means towards said disarmed position, means for latching said carrier means in said armed position against the force of said urging means and for releasing said carrier means in response to inhalation by the user such that said urging means moves said carrier means from said armed position towards said disarmed position and means for operably connecting said piston means and said carrier means to cause said piston means and said carrier means to move substantially as a unit, as said carrier means is moved toward said disarmed position by said urging means, such that said piston applies a force on a valve stem sufficient to move same to its discharge position, and to permit said piston means to move relative to said carrier means, after said carrier means has moved to said disarmed position, to automatically release said applied force.

11. The apparatus of claim 10 wherein said housing has an air passageway therein and said latch means comprises a door mounted for movement in said housing between a position substantially obstructing the passageway and a substantially non-obstructing position.

12. The apparatus of claim 11 wherein said latch means further comprise toggle means operably connecting said carrier means and said housing, said toggle means being movable between a latched position, wherein said carrier means is retained in said armed position, and a position wherein said carrier means is released.

13. The apparatus of claim 12 further comprising means for operably latching said door in said obstructing position.

14. The apparatus of claim 13 wherein said toggle means comprises a first element and a second element, means for pivotally mounting one end of said first element on said carrier means for movement about a first axis, means for pivotally mounting one end of said second element on said housing for movement about a second axis and means for pivotally connecting another end of said first element and another end of said second element for movement about a third axis.

15. The apparatus of claim 14 wherein said door and said toggle means retain said carrier means in a latched position when said door is in said substantially obstructing position.

16. The apparatus of claim 14 wherein said first axis, said second axis and said third axis are substantially co-linear when said toggle means is in said latched position.

17. The apparatus of claim 10 wherein said housing comprises first and second parts moveable relative to each other to move said carrier means from said disarmed position to said armed position, against the action of said urging means.

18. The apparatus of claim 17 wherein one of said housing parts is adapted to enclose a canister and the other said parts comprises means adapted to removably retain a canister.

19. The apparatus of claim 10 wherein said piston means comprises nozzle means adapted to align with a valve stem, said nozzle means having a channel adapted to receive inhalant dispensed from a valve stem of a canister.

20. The apparatus of claim 19 wherein a valve stem of a canister is adapted to move in a given direction and wherein said channel comprises a first portion elongated in said given direction and a substantially conical portion extending in a direction substantially perpendicular to said first portion.

21. The apparatus of claim 10 further comprising means for manually releasing said latch means.

22. The apparatus of claim 21 wherein said manual releasing means is accessible from the exterior of the said housing.

* * * * *